United States Patent [19]

Wada et al.

[11] Patent Number: 4,841,145

[45] Date of Patent: Jun. 20, 1989

[54] APPARATUS FOR PREPARING SAMPLE SOLUTION FOR INFRARED SPECTROPHOTOMETER AND METHOD OF ANALYZING SAMPLE SOLUTION

[75] Inventors: Akio Wada, Hachioji; Fumiko Kakeuchi, Kokubunji; Seiji Nishizawa, Tokyo, all of Japan

[73] Assignee: Nihon Bunko Kogyo Kabushiki Kaisha, Tokyo, Japan

[21] Appl. No.: 63,908

[22] Filed: Jun. 18, 1987

[30] Foreign Application Priority Data

Jun. 24, 1986 [JP] Japan .................................. 61-147393

[51] Int. Cl.$^4$ ........................ G01J 3/42; G01N 21/35
[52] U.S. Cl. .................................... 250/304; 250/341; 356/36; 356/244
[58] Field of Search ................... 250/304, 432 R, 328, 250/341, 359.1; 356/36, 38, 244

[56] References Cited

U.S. PATENT DOCUMENTS

| | | | |
|---|---|---|---|
| 3,448,268 | 6/1969 | Proctor | 250/358.1 |
| 3,614,230 | 10/1971 | Crawford | 356/38 |
| 4,349,510 | 9/1982 | Kolehmainen et al. | 356/244 |

OTHER PUBLICATIONS

Gagel & Biemann, Continuous Recording of Reflection-Absorbance Fourier Transform Infrared Spectra of the Effluent of a Microbore Liquid Chromatograph Anal Chem, Sep. (1986), vol. 58, pp. 2184-2189.
Johnson et al, "Normal-Phase Liquid Chromatography/Fourier Transform . . . ", Analytical Chemistry, vol. 55, No. 3, Mar. 1983, pp. 436-441.
Brown et al, "Microbore Liquid Chromatography with Flow Cell Fourier Transform Infrared Spectrometric Detection", Analytical Chemistry, vol. 55, No. 9, 1983, pp. 1492-1497.
Johnson et al, "Zero Dead Volume Flow Cell for Microbore Liquid Chromatography with Fourier Transform . . . ", Analytical Chemistry, vol. 56, No. 14, 1984, pp. 2642-2647.
Hellgeth et al, "Optimization of a Flow Cell Interface for Reversed-Phase Liquid Chromatography/Fourier Transform . . . ", Analytical Chemistry, vol. 59, No. 2, 1987, pp. 295-300.
Jinno et al, "Combination of Micro High Performance Liquid Chromatography and Fourier Transform Infrared Spectrometry . . . ", Short Communications, School of Materials Science, Toyohashi University of Technology, Toyohashi, Japan, 1981.
Kuehl et al, "Microcomputer-Controlled Interface between a High Performance Liquid Chromatography and a Diffuse . . . ", Analytical Chemistry, vol. 52, No. 9, 1980, pp. 1394-1399.

Primary Examiner—Carolyn E. Fields
Attorney, Agent, or Firm—Browdy and Neimark

[57] ABSTRACT

A method of analyzing a sample solution comprises the steps of allowing the sample solution to drip onto a sample retaining means, depositing a solute of the sample solution by evaporating a solvent thereof, irradiating infrared radiation onto this solute, and measuring the intensity of the infrared radiation which is reflected by the solute and the sample retaining means disposed under the solute so as to obtained an infrared spectrum. An apparatus for preparing a sample solution is provided for carrying out the above-described method. In this apparatus, the sample retaining means is moved so that a layer of solute which corresponds to each droplet of sample solution is continuously formed on the sample retaining means.

14 Claims, 7 Drawing Sheets

ABSTRACT

APPARATUS FOR PREPARING SAMPLE SOLUTION FOR INFRARED SPECTROPHOTOMETER AND METHOD OF ANALYZING SAMPLE SOLUTION

BACKGROUND OF THE INVENTION

1. Field of the Invention:

The present invention relates to an apparatus for preparing a sample solution for an infrared spectrophotometer, in particular a solution from a liquid chromatograph, and a method of analyzing the sample solution.

2. Prior Art:

Apparatuses for measuring the infrared spectra of components separated by a liquid chromatograph, by using an infrared spectrophotometer disposed at the detection section of the liquid chromatograph, generally employ a flow cell (References: (1) C. C. Johnson & L. T. Taylor, Anal. Chem., 55, 436 (1983), (2) R. S. Brown, Anal. Chem., 55, 1492 (1983), (3) C. C. Johnson & L. T. Taylor, Anal. Chem., 56, 2642 (1984), and (4) L. T. Taylor, el. al., Anal. Chem., 59, 295 (1987)). In such an apparatus, a column effluent is led into the flow cell, infrared radiation is irradiated onto this flow cell, and the intensities of the infrared radiation which has been transmitted through the flow cell are measured by an infrared spectrophotometer to obtain its spectra.

This apparatus enables continuous and automatic measurement of the infrared spectra.

However, it has a disadvantage in that any kind of solvent employed in this apparatus also absorbs radiation in the infrared region. This limits the wavelength regions and the types of solvent that can be used in the measurement. Further, the material of the window of the flow cell is restricted in terms of its transmittance of infrared radiation, thereby limiting the wavelengths that can be used in the measurement.

In order to obviate these problems, a method of measuring an infrared spectrum has been proposed in which a sample solution is allowed to drip onto a sample retaining board made of crystals of KBr which transmits infrared radiation, a solvent in each droplet is evaporated to deposit a solute, and infrared radiation is transmitted through the solute to measure an infrared spectrum (Reference: K. Jinno & C. Fujimoto, HRC & CC., 4, 532 (1981)).

In this method, however, the sample solution inevitably expands on the retaining board. It is therefore necessary to greatly reduce the flow rate of the mobile phase in the liquid chromatograph, thereby limiting the amount of sample which can be used in the measurement of the infrared spectra. Further, KBr is a deliquescent substance, so it must be preserved in a dry atmosphere. If a retaining board made of KBr is employed, a solvent like water cannot be used as the mobile phase. KBr absorbs radiation in the far infrared region, so the KBr retaining board cannot be used for the measurement of a sample which shows absorption in the far infrared region (the wavenumber region of 400 cm$^{-1}$ or less). The size of this sample retaining board is limited in terms of its manufacture, handling, and preservation. This prevents continuous, automatic measurement of the infrared spectra over a long period of time (for example, for an entire day).

A diffuse reflectance method has also been known, in which diffuse reflection cups used for retaining samples, and which contain NaCl, KBr, of CaF$_2$, are aligned on a conveyor, the column effluent is sequentially allowed to drip into each of these cups, and a solvent of each droplet of sample solution is evaporated to deposit a solute (Reference: D. T. Kuehl & P. R. Griffitho, Anal, Chem., 52, 1394 (1980)).

This method requires the use of NaCl, CaF$_2$, or other substances, and the maximum number of cups which can be prepared at one time is limited to about 50. Therefore, the infrared spectra cannot be measured continuously and automatically over a long period of time.

SUMMARY OF THE INVENTION

Accordingly, an object of the present invention is to provide an apparatus for preparing a sample solution for an infrared spectrophotometer and a method of analyzing the sample solution, which do not limit the type of solvent or wavelength region that can be employed in the measurement.

Another object of the present invention is to provide an apparatus for preparing a sample solution for an infrared spectrophotometer and a method of analyzing the sample solution, which are easy to handle, and which enable the continuous automatic measurement of the infrared spectra during preparation of the samples.

To this end, the present invention provides a method of analyzing a sample solution which comprises the steps of: allowing the sample solution to drip onto sample retaining means having a surface made of substance which reflects infrared radiation; depositing a solute of the droplet of sample solution by evaporating a solvent thereof; and irradiating infrared radiation onto the deposited solute and measuring the intensity of the infrared radiation which is reflected by the solute and the sample retaining means under the solute, so as to obtain the infrared spectrum.

To carry out the above-described method, the present invention also provides an apparatus for preparing a sample solution for an infrared spectrophotometer which comprises: sample retaining means made of a substance which reflects infrared radiation; a dropping tube disposed above the sample retaining means, from which the sample solution is allowed to drip onto the sample retaining means after flowing therethrough; driving means for moving the sample retaining means continuously or intermittently; and solvent removing means for depositing a solute on the sample retaining means by evaporating a solvent of each droplet of the sample solution.

BRIEF DESCRIPTION OF THE DRAWINGS

FIGS. 4 (A) to (C) are longitudinal sectional views of part of the sample retaining tape, illustrating changes in the shape of the droplets of sample solution which have been dripped onto the sample retaining tape;

DESCRIPTION OF THE PREFERRED EMBODIMENTS

Experiments have been conducted to show that the sample solution preparing method according to this invention ensures that the components contained in a sample solution can be specified as effectively as in the prior art. The procedure and results thereof will first be described below.

Figure 10:
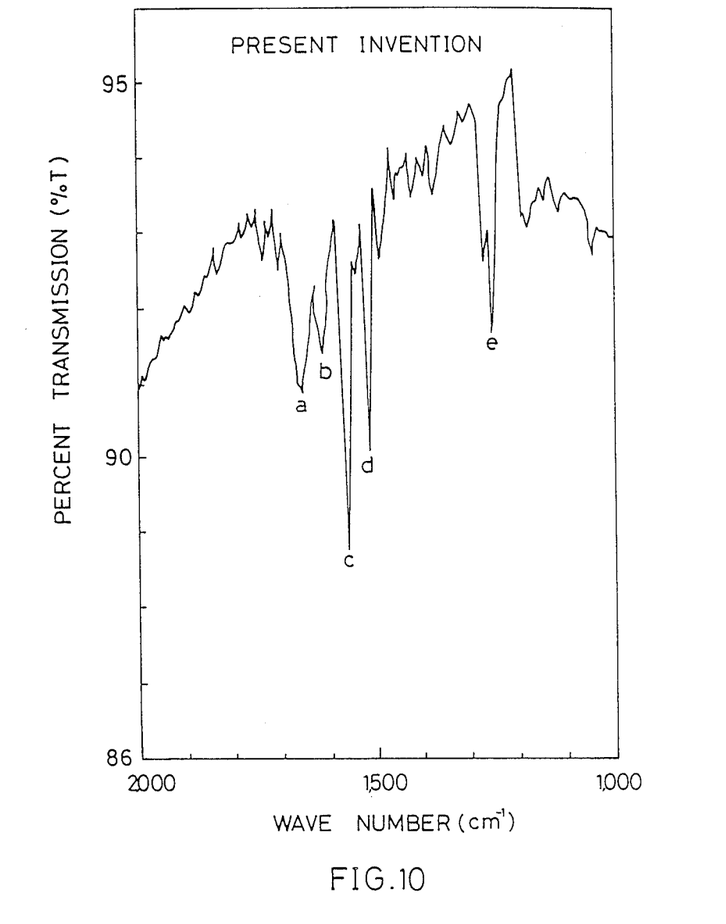
FIG. 10 shows an infrared spectrum obtained by the method according to the present invention.

A circular recess having a diameter of 5.8 mm and a depth of 1.5 mm was formed in an aluminum plate, and 2 $\mu l$ of a dichloromethane solution containing 200 ng of phenacetin was allowed to drip into this recess. The dichloromethane was then evaporated to deposit the phenacetin, infrared radiation was irradiated onto the layer of phenacetin, and the radiation which was reflected thereby was supplied to an infrared spectrophotometer which measured the infrared spectrum thereof. FIG. 10 shows the results of the measurement.

Figure 11:
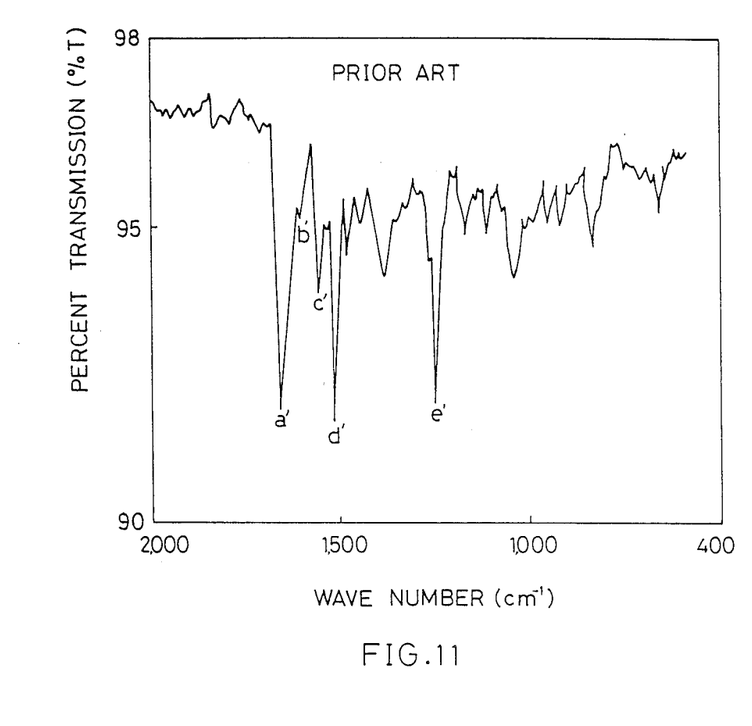
FIG. 11 shows an infrared spectrum obtained by employing the known method of diffuse reflectance, as comparison with that shown in FIG. 10.

Next, the infrared spectrum of 200 ng of phenacetin was measured by the diffuse reflectance method of the prior art and using the same infrared spectrophotometer as that used in the first measurement. FIG. 11 shows the results of the measurement.

The ordinate in both graphs indicates the percent transmission (% T), and the abscissa shows the wave number ($cm^{-1}$). Absorption band peaks, a, b, c, d, and e in FIG. 10 respectively correspond to absorption band peaks, a', b', c', d', and e' in FIG. 11.

It is apparent from the two graphs that the method according to the present invention enables the components in the sample solution to be specified as effectively as in the prior art.

The method of the present invention can eliminate the use of a powder, such as KBr or $CaF_2$, which is required in the known diffuse reflectance method, and is therefore easy to handle.

In the method of this invention, since the solvent is evaporated, the type of solvent which is employed or the wavelength region to be used is not limited.

Part of the infrared radiation which has transmitted through the layer of sample is reflected back by the surface of the aluminum plate, and is transmitted again through the layer of sample. This means that the intensity of radiation which has been transmitted through a layer of sample which is twice as thick is measured. The amount of sample solution to be dripped can thereby be reduced.

A first embodiment of the present invention will now be described by referring to FIGS. 1 to 5 and FIGS. 12 and 13.

Figure 1:
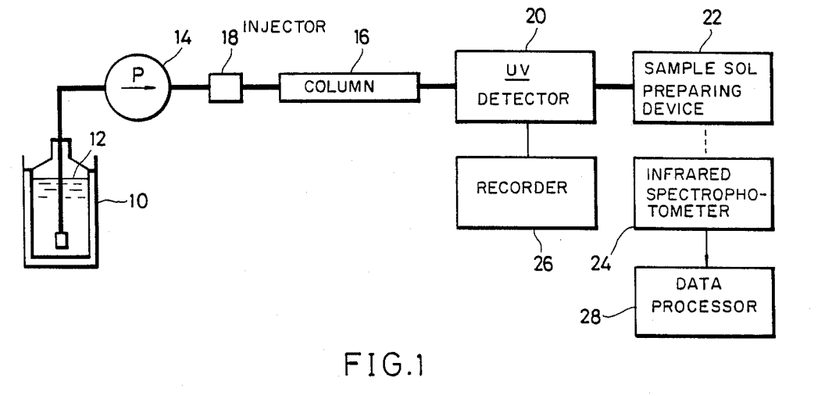
FIG. 1 is a block diagram of a first embodiment of a sample solution preparing apparatus according to the present invention, showing the entire arrangement thereof.

Referring first to FIG. 1, which schematically shows the entire construction of the apparatus, a mobile phase 12 contained in a reservoir 10 is fed to a column 16 by a pump 14. A sample is injected into the column 16 by an injector 18. A column effluent passes through a UV detector 20, is then supplied to a sample solution preparing device 22 as a sample solution, and the infrared spectra thereof are measured by an infrared spectrophotometer 24. A recorder 26 records ultraviolet absorbances measured by the UV detector 20, and a data processor 28 records the measured infrared spectra.

Figure 2:
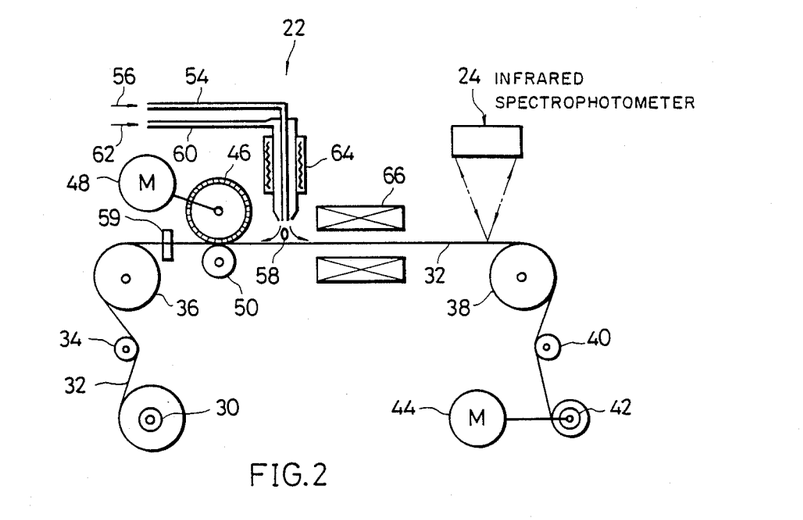
FIG. 2 is a schematic view of the sample preparing device of FIG. 1, showing the entire arrangement thereof.
Figure 3:
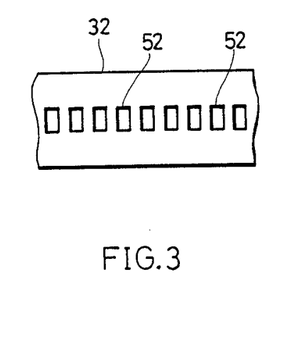
FIG. 3 is a plan view of part of the sample retaining tape of FIG. 2 which is provided with recesses.

Turning to FIG. 2, which shows the sample solution preparing device 22, a sample retaining tape 32 which has been wound around a core 30 is unwound therefrom, and is fed around a tension roller 34, guide rollers 36, 38 and a tension roller 40 in sequence, before being wound around a core 42. The core 42 is driven by a motor 44. The sample retaining tape 32 is made of a thin plate of a metal which is corrosion proof and which reflects infrared radiation, such as thin aluminum plate. This thin aluminum plate may have a thickness of 0.2 mm.

Between the guide rollers 36 and 38 are disposed a forming roller 46 and a rubber press roller 50 which is pressed against the forming roller 46 with the sample retaining tape 32 therebetween. The forming roller 46 is driven by a motor 48 so as to feed the sample retaining tape 32 towards the guide roller 38 at a fixed speed. The center of the outer periphery of the forming roller 46 is provided with a plurality of elongated protrusions (not shown) which are spaced equally round the circumference thereof, by which recesses 52 (shown in FIG. 3) are formed in the sample retaining tape 32 when it is located between these protrusions and the rubber press roller 50. Each of the recesses 52 may have a dimensions of 3 mm × 5 mm and a depth of 0.5 mm. The width of the sample retaining tape 32 may be any value, so long as it is wider than the width of the recesses 52, and may be 20 mm.

Between the guide roller 38 and the forming roller 46 is disposed a dropping tube 54 having an end portion which is directed toward the center of the sample retaining tape 32. A sample solution 56 which has passed through the UV detector 20 flows through the dropping tube 54, and drops from the end opening thereof onto the upper surface of the sample retaining tape 32 as a droplet 58. The end portion of the dropping tube 54 is covered by an end portion of a gas tube 60 which is disposed coaxially with the end portion of the dropping tube 54. Dry nitrogen gas 62 flows through the gas tube 60 and is emitted from the end opening thereof. The end portion of the gas tube 60 is covered by a heater 64 which increases the temperature of the dry nitrogen gas 62 as it passes therethrough. The droplet 58 allowed to drip onto the sample retaining tape 32 is accordingly exposed to an atmosphere which promotes the evaporation of the solvent, so that part of the solvent is evaporated.

A cleaner 59 for removing dust attached to the sample retaining tape is disposed between the guide roller 36 and the forming roller 46. The cleaner 59 may be constructed by sponges which are disposed above and under the sample retaining tape in such a manner as to grip the tape, by the blowing of dry nitrogen gas onto the sample retaining tape 32, or by suction with negative pressure.

Between the end portion of the gas tube 60 and the guide roller 38 is disposed a high-frequency heating coil 66 through which the sample retaining tape 32 is passed. The dry nitrogen gas 62 also passes through the hollow portion of the high-frequency heating coil 66, so that the droplet 58 is still exposed to the atmosphere which promotes the evaporation of the solvent while it is located in the hollow portion of the heating coil. As the droplet 58 passes through the hollow portion of the high-frequency heating coil 66, the corresponding part of the sample retaining tape is heated, heating the droplet 58 indirectly, and thereby fully evaporating the solvent of the droplet 58. The sample retaining tape 32 transfers heat, and the part of the sample retaining tape 32 which is located just under the droplet 58 is also heated, accelerating the evaporation of the solvent. The power to be supplied to the high-frequency heating coil 66 mainly depends on the volatility of the solvent. In some case, it could even be unnecessary to supply power to the coil.

Figure 4A:
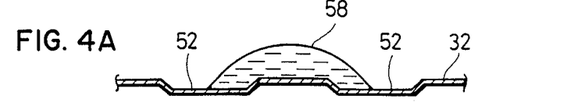
Figure 4B:
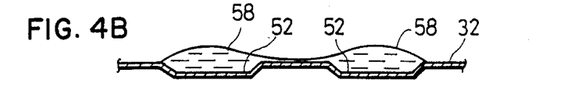
Figure 4C:
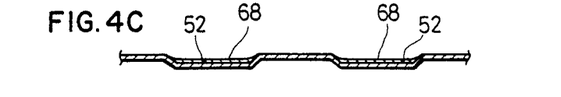

If the droplet 58 is allowed to drip midway between adjacent recesses 52 formed in the sample retaining tape 32, it has a form shown in FIG. 4 (A). When the dry nitrogen gas 62 is blown onto the droplet 58 in that state from above, most of the droplet 58 moves into the adjacent recesses 52, as shown in FIG. 4 (B). This prevents the droplet 58 from expanding too far and thinning out too much, and the amount of sample solution in each droplet can be reduced. Accordingly, the degree of mixture of different components can be reached. Next, when the solvent in the droplet 58 has been evaporated by the passing through the high-frequency heating coil 66, a layer of solute 68 separates out on the bottom of the each recess 52, as shown in FIG. 4 (C). The diameters of the particles of the solute 68 differ, even if only a single type of solute is present.

Figure 5:
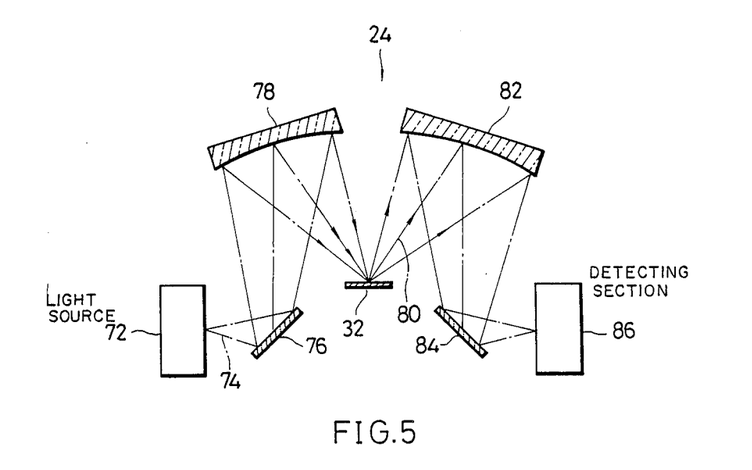
FIG. 5 is a sectional view of an optical system disposed near the sample section of an infrared spectrophotometer of FIG. 2.

An infrared spectrophotometer 24 is disposed at the exit of the high-frequency heating coil 66. The infrared spectrophotometer 24 includes, as shown in FIG. 5, a light source 72, a plane mirror 76 for changing the direction of infrared radiation 74 irradiated from the light source 72, a concave mirror 78 for condensing received infrared radiation 74 onto the center of the sample retaining tape 32, a concave mirror 82 for condensing infrared radiation 80 which has been reflected by the solute 68 on the sample retaining tape 32, a plane mirror 84 for changing the direction of the reflected radiation from the concave mirror 82, and a detecting section 86 into which the reflected radiation from the plane mirror 84 enters after being collected by the passing through an entrance slit.

Part of the infrared radiation 74 which has been irradiated by the infrared spectrophotometer is transmitted through the solute 68, is reflected by the bottom of the recess 52, and is transmitted back through the solute 68. The solute 68 absorbs part of that infrared radiation while it is transmitted therethrough. The thickness of the solute layer 68 is determined so that a sufficient amount of incident infrared radiation can reach the bottom of the recess 52. In general, it can be as thick as a molecular layer or more, which is up to about 100 $\mu$m. In practice, the thickness of the solute 68 is between 10 and 20 $\mu$m.

The apparatus of this embodiment does not require the use of KBr or other substances. The use of the sample retaining tape makes it possible for the infrared spectra to be measured continuously and automatically over a long period of time while the sample is being prepared.

Tests were conducted by using the apparatus of this embodiment, and the results thereof are described below. Chloroform was fed at a flow rate of 0.2 m l/min as the mobile phase 12 in order to enable the analysis of a polystyrene oligomer as the sample.

Devices employed in the tests were those manufactured by Japan Spectroscopic Co., Ltd. (JASCO), as listed below:
Pump 14: TRIROTAR-V,
Column 16: Finepack GEL 101 (46 mm I.D. $\times$ 500 mm L),
Injector 18: VL-614,
UV detector 20: UVIDEC-100-V,
Infrared Spectrophotometer 24: FT/IR-5M.

Figure 12:
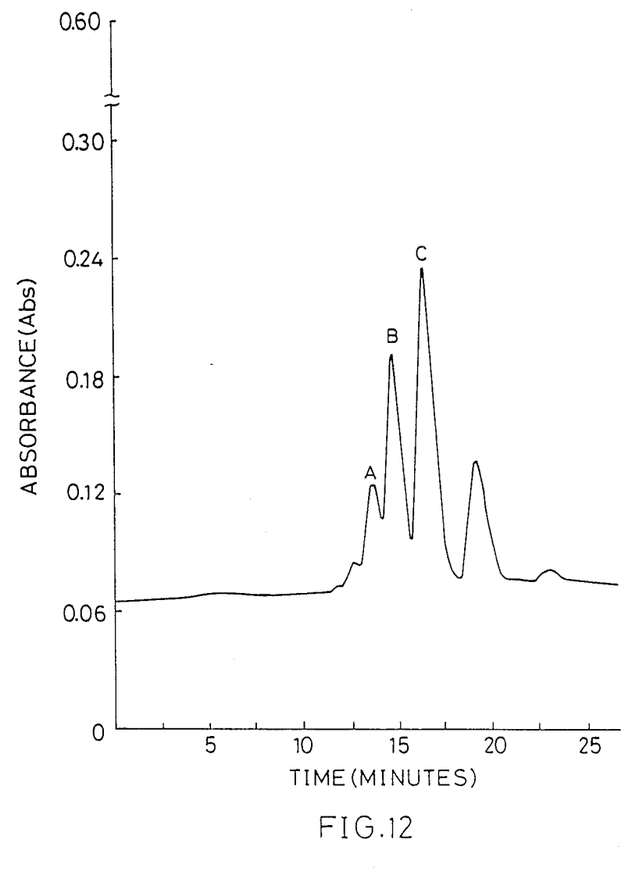
FIG. 12 is a chromatogram obtained by recording the signals delivered from the UV detector 20 of FIG. 1 by the recorder 26.
Figure 13:
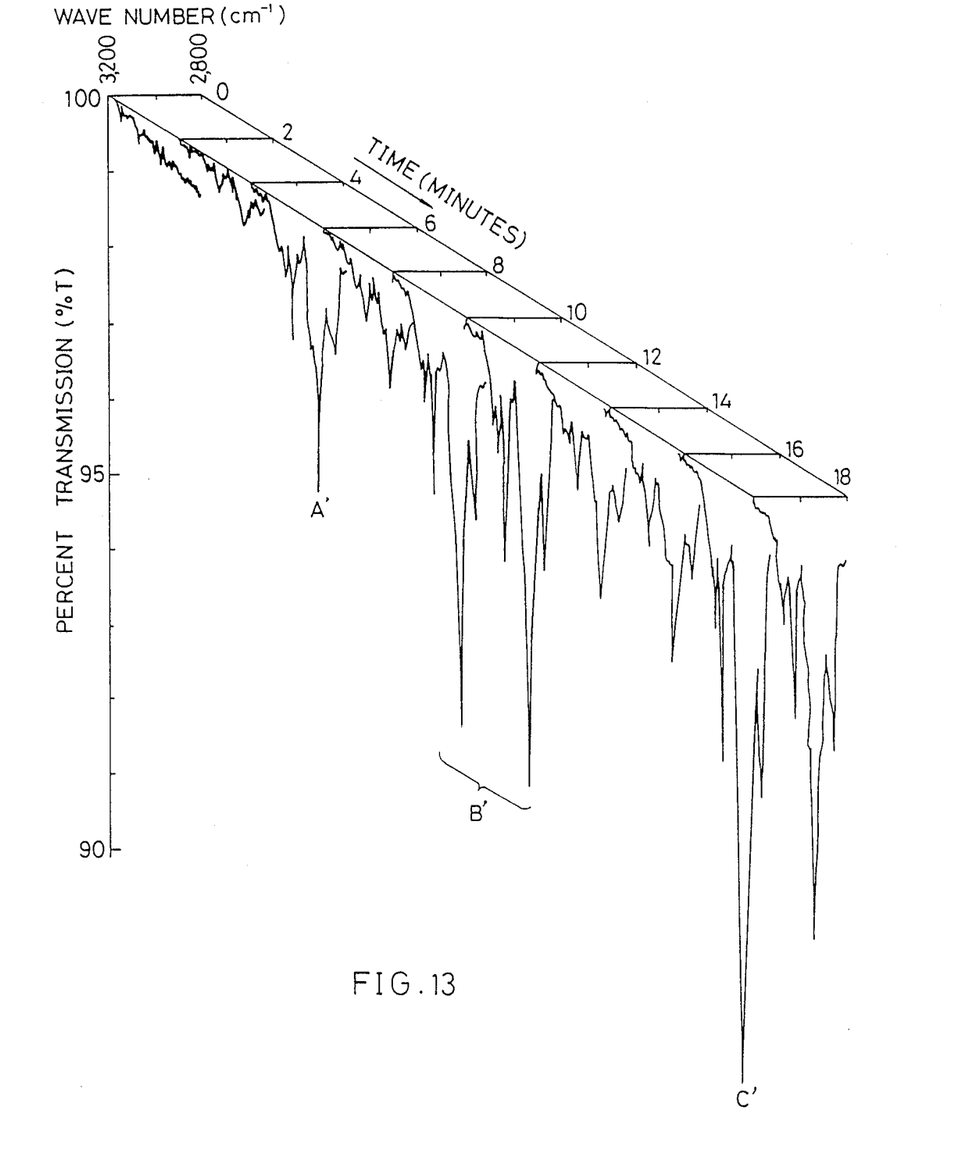
FIG. 13 is infrared spectra recorded by the data processor 28 of FIG. 1 at fixed intervals.

FIGS. 12 and 13 show the results of the measurements.

FIG. 12 is a chromatogram obtained from the measurements performed by the UV detector 20. The abscissa of the graph indicates time (minute), and the ordinate thereof denotes absorbance (Abs). The wavelength of the ultraviolet radiation employed was 280 nm.

FIG. 13 shows the infrared spectra of the solutes 68 deposited in the recesses 52 which were measured by the infrared spectrophotometer 24 at fixed intervals. The ordinate of the graph indicates the percent transmission (% T), and one abscissa thereof shows wave number (cm$^{-1}$), while the other abscissa shows time.

Absorption band peaks A, B, and C in FIG. 12 correspond to absorption band peaks A', B', and C' in FIG. 13, respectively.

Figure 6:
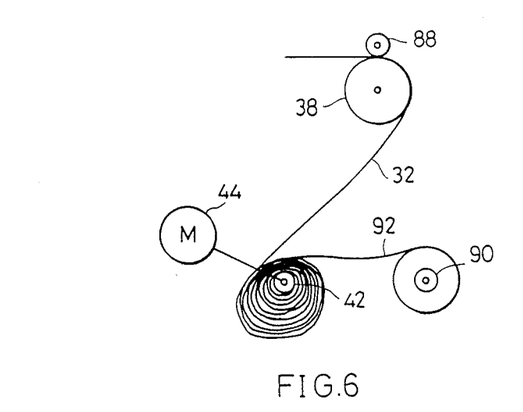
FIG. 6 is a schematic view of part of a sample preparing device, showing a second embodiment of the present invention.

Next, a second embodiment of this invention will now be described by referring to FIG. 6.

The rotational force of the forming roller 46 shown in FIG. 2 is transmitted to the guide roller 38 via a belt (not shown) so as to rotate it together with the forming roller 46. A rubber press roller 88 is pressed against the outer periphery of the guide roller 38 with the sample retaining tape 32 therebetween. These make the sample retaining tape 32 located between the forming roller 46 and the guide roller 38 tightened.

After passing through the guide roller 38, the sample retaining tape 32 is wound around the core 42 loosely. The forward end of a strip of film 92 wound around a core 90 is attached to the core 42 together with the forward end of the sample retaining tape 32, so that the sample retaining tape 32 is loosely wound around the core 42 together with the film 92. Other constructions of this embodiment are the same as those of the first embodiment.

With this arrangement, the sample retaining tape 32 can be wound around the core 42 without any deformation of the recesses 52. Further, since the upper openings of the recesses 52 are covered by the film 92, the attachment of dust to the solutes 68 can be prevented. This enables preservation of the prepared samples. Other functions of this embodiment are the same as those of the first embodiment.

Figure 7:
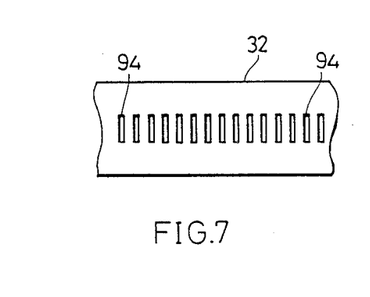
FIG. 7 is a plan view of part of a sample retaining tape having recesses which are different in shape from those formed in the sample retaining tape of FIG. 3, showing a third embodiment of the present invention.

A third embodiment of the present invention will now be described by referring to FIG. 7.

In this embodiment, recesses 94 formed in the sample retaining tape 32 have a shape which is elongated in the lateral direction thereof. The dimensions of each recess 94 may be 1.0 mm×5.0 mm×0.5 mm.

With this arrangement, the sample solution 56 can be divided into smaller droplets on the sample retaining tape 32 by reducing the diameter of the end opening of the dropping tube and by increasing the flow rate of the dry nitrogen gas. As a result, the degree of mixture of different components can be reduced, and the solvent of the droplet 58 can be quickly evaporated.

Figure 8:
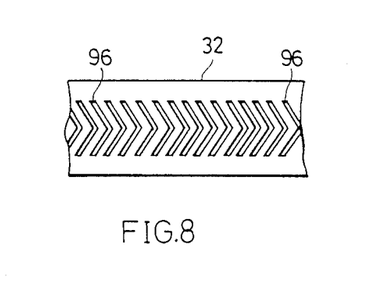
FIG. 8 is a plan view of part of a sample retaining tape having recesses which are different in shape from those formed in the sample retaining tape of FIG. 3, showing a fourth embodiment of the present invention.

A fourth embodiment of the present invention will now be described by referring to FIG. 8.

In this embodiment, recesses 96 have a shape which is bent at the center thereof in the direction of movement of the sample retaining tape. The overall length of each recess 96 is larger than that of the recess 94 shown in FIG. 7. The droplet 58 therefore expands along the recess 96, and the expansion of the droplet 58 in the longitudinal direction of the sample retaining tape 32 can be thereby prevented. As a result, the speed of movement of the sample retaining tape 32 can be slowed, thereby reducing waste of the sample retaining tape 32.

Figure 9:
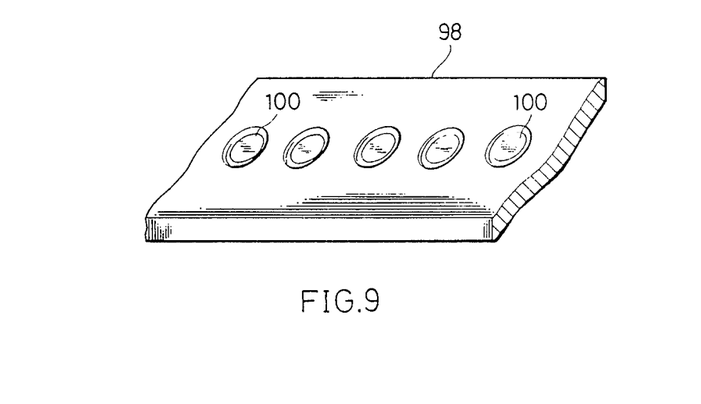
FIG. 9 is a perspective view of part of a sample retaining board, showing a fifth embodiment of the present invention.

A fifth embodiment of the present invention will now be described by referring to FIG. 9.

In this embodiment, elliptical recesses 100 are formed beforehand at the center of a sample retaining plate 98. The sample retaining plate 98 is made of aluminum. It is conveyed in the longitudinal direction on a conveyor (not shown).

The construction of the sample preparing apparatus of this embodiment can thereby be made simpler.

It is to be understood that the present invention includes various other modifications and alterations.

For example, the sample retaining means may be a rectangular aluminum plate having a plurality of recesses formed thereon in a matrix form. In this case, the aluminum plate may be moved in a direction other than the longitudinal direction thereof, to prepare samples. Alternatively, the sample retaining means may be a string of short metal plates, each metal plate having a recess, which is formed like a belt. The two ends of this string may be connected to form a loop which is rotated. Or this string may be wound around a core to be drawn therefrom, as in the case shown in FIG. 2. The sample retaining means need not be provided with recesses. The solvent removing means may be a drier which irradiates microwaves or infrared radiation. The sample solution may be a solution which is periodically extracted for inspection during the continuous manufacturing process of a single chemical. The droplets dripped from the dropping tube may be detected by a rain sensor which is usually employed to automatically operate the wipers of an automobile and which utilizes a photointerrupter, so that the infrared spectra can be measured in synchronism with this detection. The sample retaining means may also be fed intermittently.

Accordingly, all the modifications and alterations which come within the scope of the spirit of this invention are set forth in the appended claims.

What is claimed is:

1. An apparatus for measuring the infrared spectrum of a component separated by a liquid chromatograph, comprising:

sample retaining means having a surface made of a substance which reflects infrared radiation, a recessed portion being formed on said surface;

a dropping tube, having an end portion disposed above said sample retaining means, for receiving effluent from a column of a liquid chromatograph, and through which said effluent flows as a sample solution and from which said sample solution is allowed to drip into said recessed portion of said sample retaining means;

driving means for driving said sample retaining means continuously or intermittently;

solvent removing means for depositing a solute of said sample solution dripped in said recessed portion of said sample retaining means by evaporating a solvent of said sample solution; and an infrared spectrophotometer which emits infrared radiation onto the deposited solute and measures the intensity of the infrared radiation which is absorbed by said solute and reflected back through said deposited solute by a bottom surface of said recessed portion.

2. An apparatus according to claim 1, wherein said sample retaining means is a strip of plate, and the upper surface of said sample retaining means if provided with a plurality of recesses which have the same shape and which are equidistant from each other in the longitudinal direction thereof.

3. An apparatus according to claim 1, wherein said sample retaining means is a metal tape which is wound around a first core and which is drawn therefrom when it is used.

4. An apparatus according to claim 3, further comprising: a forming roller having a plurality of protrusions formed on the outer periphery thereof in such a manner that they are spaced equally around the circumference thereof; and a press roller pressed against said forming roller with said drawn metal tape therebetween, said forming roller and said press roller being disposed on the side which is closer to said core with respect to the position at which said sample solution is allowed to drip.

5. An apparatus according to claim 4, further comprising: a cleaner for removing dust attached to said metal tape.

6. An apparatus according to claim 4, further comprising: winding means for winding said metal tape onto said first core, said winding means being disposed ahead of the position from which said infrared radiation is emitted.

7. An apparatus according to claim 6, further comprising: an elongated film member drawn from a second core and wound around said first core together with said metal tape.

8. An apparatus according to claim 1, wherein said solvent removing means includes a gas tube surrounding the outer periphery of the end portion of said dropping tube, said gas tube having drying means, including an end opening of said gas tube, for blowing dry gas onto said sample retaining means.

9. An apparatus according to claim 8, wherein said drying means further includes a temperature control means for ensuring that said dry gas blown from said end opening has a temperature which is higher than the ambient temperature.

10. An apparatus according to claim 8, wherein said solvent removing means has a heating means for heating the sample solution dripped onto said sample retaining means.

11. An apparatus according to claim 1, wherein said solvent removing means has heating means for heating the sample solution which has been allowed to drip onto said sample retaining means.

12. An apparatus according to claim 1, further comprising:

means in fluid connection with a liquid chromatograph for supplying a column effluent to said dropping tube as said sample solution.

13. A method of analyzing effluent from a column of a liquid chromatograph comprising the steps of:

dripping an effluent, including a solution of a solute in a solvent, from a column of a liquid chromatograph, into a recessed portion of sample retaining means having a surface made of a substance which reflects infrared radiation;

evaporating said solvent from said sample retaining means to deposit said solute; and irradiating the deposited solute with infrared radiation wherein said infrared radiation is transmitted through said solute, then reflected by said sample retaining means below said solute, and emerges to the outside after being transmitted again through said solute;

measuring the intensity of the emerged infrared radiation to obtain an infrared spectrum.

14. A method of analyzing a sample solution according to claim 13, wherein said sample retaining means is in the form of a strip and said sample retaining means is fed in its longitudinal direction.

* * * * *